United States Patent
Zhang et al.

(10) Patent No.: US 10,412,962 B2
(45) Date of Patent: Sep. 17, 2019

(54) ANTIFUNGAL COMPOSITIONS AND METHODS OF USE THEREOF

(71) Applicants: North Carolina Agricultural and Technical State University, Greensboro, NC (US); The University of North Carolina at Greensboro, Greensboro, NC (US)

(72) Inventors: Lifeng Zhang, Oak Ridge, NC (US); Dennis R. LaJeunesse, Greensboro, NC (US); Nafisa Sirelkhatim, Greensboro, NC (US)

(73) Assignees: North Carolina Agricultural and Technical State University, Greensboro, NC (US); The University of North Carolina at Greensboro, Greensboro, NC (US)

( * ) Notice: Subject to any disclaimer, the term of this patent is extended or adjusted under 35 U.S.C. 154(b) by 13 days.

(21) Appl. No.: 15/360,068

(22) Filed: Nov. 23, 2016

(65) Prior Publication Data
US 2017/0142965 A1 May 25, 2017

Related U.S. Application Data

(60) Provisional application No. 62/259,900, filed on Nov. 25, 2015.

(51) Int. Cl.
| | | |
|---|---|---|
| A01N 43/16 | (2006.01) |
| A01N 37/34 | (2006.01) |
| C09D 5/16 | (2006.01) |
| C09D 101/12 | (2006.01) |
| C09D 7/40 | (2018.01) |
| C08K 7/02 | (2006.01) |
| C08L 1/12 | (2006.01) |
| C08L 33/20 | (2006.01) |

(52) U.S. Cl.
CPC ............. *A01N 43/16* (2013.01); *A01N 37/34* (2013.01); *C09D 5/1637* (2013.01); *C09D 7/70* (2018.01); *C09D 101/12* (2013.01); *C08K 7/02* (2013.01); *C08L 1/12* (2013.01); *C08L 33/20* (2013.01)

(58) Field of Classification Search
None
See application file for complete search history.

(56) References Cited

U.S. PATENT DOCUMENTS

| | | |
|---|---|---|
| 5,533,731 A | 7/1996 | Koenig |
| 5,602,097 A | 2/1997 | Edwards |
| 5,885,782 A | 3/1999 | Edwards |
| 6,020,312 A | 2/2000 | Edwards |
| 2004/0006826 A1* | 1/2004 | Mao .............. A01N 47/22 8/115.51 |
| 2005/0197319 A1* | 9/2005 | Nonomura ........... A61K 8/0208 514/57 |
| 2010/0015045 A1 | 1/2010 | Young et al. |
| 2010/0285081 A1* | 11/2010 | Chen .................... D01D 5/0038 424/405 |

FOREIGN PATENT DOCUMENTS

EP    2 431 429    3/2012

OTHER PUBLICATIONS

Sirelkhatim, N., et al., Materials Letters 141: 217-220 (available online Nov. 26, 2014).*
Tolnaftate, accessed from the Internet on Oct. 13, 2017 from https://en.wikipedia.org/wiki/Tolnaftate.*
"Chlorhexidine," retrieved from the Internet on May 11, 2018, from <<https://en.wikipedia.org/wiki/Chlorhexidine>>. (Year: 2018).*
Canbolat et al., "Preservation of Cell Viability and Protein Conformation on Immobilization within Nanofibers via Electrospinning Functionalized Yeast," ACS Appl. Mater. Intercaes 2013, 5, 9349-9354.
Dixit et al., "Fungal Growth Inhibition of Regenerated Cellulose Nanofibrous Membranes Containing Quillaja Saponin," Arch. Environ. Contam. Toxicol. (2010) 59:417-423.
Lala et al., "Fabrication of Nanofibers With Antimicrobial Functionality Used as Filters: Protection Against Bacterial Contaminants," Biotechnology and Bioengineering, vol. 97, No. 6, pp. 1357-1365 (Aug. 15, 2007).
Lemma et al., "Removal of bacteria and yeast in water and beer by nylon nanofibrous membranes", Journal of Food Engineering 157 (2015) 1-6.
Magill et al., "Multistate point-prevalence survey of health care associated infections." The New England Journal of Medicine, vol. 370, pp. 1198-1208 (2014).
Santos et al., "Antifungal effect of electrospun nanofibers containing cetylpyridinium chloride against Candida albicans," Braz Oral Res., (São Paulo) 2014;28(1):1-6.
Sun et al., "Electrospun Composite Nanofiber Fabrics Containing Uniformly Dispersed Antimicrobial Agents As an Innovative Type of Polymeric Materials with Superior Antimicrobial Efficacy," Applied Materials & Interfaces, vol. 2, No. 4, pp. 952-956 (2010).
Zhang et al., "Antimicrobial nano-fibrous membranes developed from electrospun polyacrylonitrile nanofibers," Journal of Membrane Science 369 (2011) 499-505.

* cited by examiner

*Primary Examiner* — David J Blanchard
*Assistant Examiner* — Daniel F. Coughlin
(74) *Attorney, Agent, or Firm* — Jenkins, Wilson, Taylor & Hunt, P.A.

(57) ABSTRACT

The presently disclosed subject matter relates generally to antifungal nanofibrous materials and the use of such materials.

10 Claims, 5 Drawing Sheets

ANTIFUNGAL COMPOSITIONS AND METHODS OF USE THEREOF

CROSS REFERENCE TO RELATED APPLICATIONS

This application claims priority pursuant to 35 U.S.C. § 119(e) to U.S. Provisional Patent Application Ser. No. 62/259,900, filed on Nov. 25, 2015, which is hereby incorporated by reference in its entirety.

TECHNICAL FIELD

The presently disclosed subject matter relates generally to antifungal materials comprising nanofibers, such as polyacrylonitrile nanofibers and/or cellulose acetate nanofibers, and the use of such materials.

BACKGROUND

Fungi are abundant in the world and play a major role in decomposing organic matter. While some fungi species are valuable, e.g. *Saccharomyces cerevisiae* (*S. cerevisiae*) which is widely used in fermentation, many species of fungi including molds and mildews can spoil and/or damage indoor and outdoor surfaces. Many fungi produce allergens and toxins that can harm humans, animals and plants. *Candida albicans* (*C. albicans*) can lead to infection, candidiasis (e.g. thrush, yeast infections, and onychomycosis), in humans. The Centers for Disease Control and Prevention has reported that *Candida* is the "most common cause of healthcare-associated bloodstream infections in the United States" (cdc.gov/fungal/antifungal-resistance.html, citing to Magill, S. S., Edwards J. R., Bamberg, W., et al. "Multistate point-prevalence survey of health care-associated infections." The New England Journal of Medicine 2014; 370: 1198-208). Uncontrolled fungal growth is both an environmental concern and a health concern. In particular, it is important to address the potential growth and transfer of fungi in textiles, such as those found in hospitals, hotels, offices, homes, retirement communities, and military settings.

To fight fungi, a variety of antifungal reagents have been developed, however most are non-specific. A number of chemical agents have been shown to have antifungal activity, but can be detrimental to the environment—toxic to plants, animals and humans. Additionally, use of antifungal drugs may take long time and side-effects can be an issue. Fungi have also been known to develop resistance to antifungal drugs, such as fluconazole and echinocandins. A straightforward and effective alternative to conventional antifungal reagents is needed to limit the spread and impact of fungi.

SUMMARY

The nanofibers of the presently disclosed subject matter have been shown to have antifungal activity.

In some aspects, the presently disclosed subject matter provides a surface coating composition comprising nanofibers of polyacrylonitrile (PAN and/or cellulose acetate (CA) in an amount sufficient to inhibit or prevent the growth of a fungus on a surface coated with said surface coating composition. In some embodiments, the presently disclosed subject matter provides an antifungal surface treated with PAN nanofibers and/or CA nanofibers. In some embodiments, the antifungal surface is treated with an antifungal effective amount of nanofibers of polyacrylonitrile and/or cellulose acetate.

In some aspects, the presently disclosed subject matter provides a method for the antifungal treatment of a surface comprising applying an antifungal effective amount of a composition comprising nanofibers of polyacrylonitrile and/or cellulose acetate to a surface in need of such antifungal treatment. In some embodiments, the presently disclosed subject matter provides for the use of polyacrylonitrile nanofibers and/or cellulose acetate nanofibers on a surface, including but not limited to an indoor or outdoor surface: textiles, shoes, furniture, building, plants or any surface on which fungi can grow.

These and other embodiments are described in greater detail in the detailed description which follows.

Accordingly, it is an object of the presently disclosed subject matter to provide nanofibers having antifungal activity.

An object of the presently disclosed subject matter having been stated hereinabove, and which is achieved in whole or in part by the presently disclosed subject matter, other objects will become evident as the description proceeds when taken in connection with the accompanying drawings as best described herein below.

DETAILED DESCRIPTION

Figure 1A:
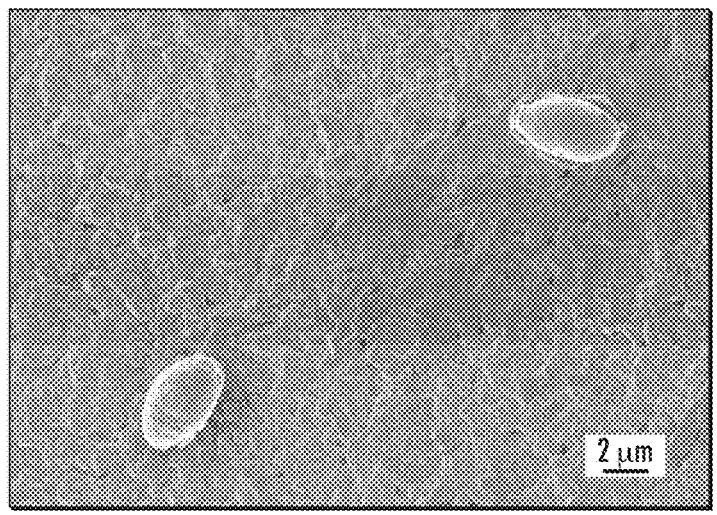
FIG. 1A illustrates a scanning electron microscope (SEM) image of yeast cells cultured on a PAN substrate after 30 min incubation wherein the PAN substrate is a PAN solid film.

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or."

As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed subject matter can include the use of either of the other two terms.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10", "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

As used herein, "nanofibers" or "nanofibrous" refers to fibers with diameters from about 100 nm to about 1000 nm. The nanofibers described herein generally are typically prepared by electrospinning of spin dope comprising polyacrylonitrile (PAN) or cellulose acetate (CA). Alternate methods of preparation of nanofibers are known in the art. In some embodiments, the nanofibers are characterized by average diameters of no more than about 750 nm, no more than about 500 nm, no more than about 250 nm. In other embodiments, the nanofibers are characterized by average diameters of between about 100 nm to about 250 nm, or between about 100 nm to about 500 nm, or between about 100 nm to about 750 nm, or between about 250 nm and about 750 nm or between about 300 nm and 700 nm or between about 400 nm and about 600 nm.

As used herein an "antifungal effective amount" of an antifungal composition refers to a composition comprising an amount of nanofibers of polyacrylonitrile and/or nanofibers of cellulose acetate sufficient to inhibit growth of fungus.

As used herein, "inhibit growth of fungus" means that the growth of fungus in the presence of the nanofibers disclosed herein is slower than the growth of fungus not in the presence of the nanofibers. In one variation, inhibition of growth reflects that the presence of nanofibers kills fungal cells, thereby reducing its growth. In one aspect, the growth of fungus is slowed in the presence of the nanofibers disclosed herein, where fungal cell growth is measured by a typical approach, such as $OD_{600}$ of cell culture, where a lower $OD_{600}$ corresponds to the presence of fewer cells and correspondingly a higher cell inhibition effect. Alternately, fungal cell growth is halted, wherein no additional growth of fungus is observed after the application of the nanofibers disclosed herein, e.g. no additional cell growth is measured. In another alternative, the growth of fungus is reversed, such that existing or applied fungal cells are killed due to or die in the presence of the nanofibers disclosed herein.

In some embodiments, the growth of fungi in the presence of the nanofibers of the present application is demonstrably slowed and/or fungi are killed when the fungal cell viability, as represented by the $OD_{600}$ of the solution of fungi exposed to nanofibers of the present application is no more than about 75% of the $OD_{600}$ of the (control) solution of fungi not exposed to nanofibers of the present application. Alternately, the $OD_{600}$ of the exposed fungi solution is no more than about 60%, no more than about 50%, no more than about 40%, no more than about 30%, no more than about 20% or no more than about 10% of the $OD_{600}$ of the exposed fungi solution. In some embodiments, the growth of fungi in the presence of the nanofibers of the present application is demonstrably slowed and/or fungi are killed when the normalized Colony Forming Unit ratio (CFU) of fungi exposed to nanofibers of the present application is no more than about 60% of the CFU of (control) fungi not exposed to nanofibers of the present application. Alternately, the CFU of the exposed fungi is no more than about 50%, no more than about 40%, no more than about 30%, no more than about 25%, no more than about 20%, no more than about 15%, or no more than about 10% the CFU of unexposed fungi. In other embodiments, the growth of fungi in the presence of the nanofibers of the present application is demonstrably slowed and/or fungi are killed when the metabolic activity, as represented by MTT absorbance in an MTT assay, of the fungi exposed to nanofibers of the present application is no more than about 50% of the MTT absorbance of (control) fungi not exposed to nanofibers of the present application. Alternately, the MTT absorbance of the exposed fungi is no more than about 40%, no more than about 35%, no more than about 30%, no more than about 25%, no more than about 20%, no more than about 15%, or no more than about 10% the MTT absorbance of unexposed fungi.

As used herein, "exposed to fungus" means that fungal cells come in physical contact with the presently disclosed nanofibers. In some variations, fungal cells are in a solution that comes in contact with a composition comprising the nanofibers of the present application. In another variation, the fungi As disclosed herein, the interactions between each of PAN nanofibers and CA nanofibers with baker's yeast, *Saccharomyces cerevisiae*, and with *Candida albicans* were investigated. *S. cerevisiae* is a model genetic microorganism and type of fungus central to the fermentation industry; *C. albicans* is a dimorphic fungus responsible for candidiasis in humans. As disclosed herein, nanofibrous PAN and nanofibrous CA adversely affected the growth, morphology, and viability of these representative fungi. The demonstrated antifungal activity of PAN nanofibrous mats was in contrast to both PAN film and PAN microfibrous mats, neither of which demonstrated the same antifungal activity. Similarly, CA nanofibers demonstrated antifungal activity, while a CA cast film did not lead to decreased cell viability. As reported herein, antifungal activity of other nanofibrous mats prepared from a variety of starting materials, including amidoxime surface modified PAN, carbon, cellulose, cellulose with embedded $TiO_2$ (Cellulose_$TiO_2$), and cellulose acetate with embedded $TiO_2$ (CA_$TiO_2$) were also investigated. Each of PAN nanofibers and CA nanofibers demonstrated notable antifungal activity. Further, nanofibrous PAN and nanofibrous CA demonstrated antifungal activity without the addition of separate agents, such as amidoxime, or metal centers, including but not limited to $TiO_2$. Notably, nanofibrous CA demonstrated increased antifungal activity compared to CA with embedded $TiO_2$ (CA_$TiO_2$).

In some aspects, the presently disclosed subject matter provides a surface coating composition comprising nanofibers of polyacrylonitrile and/or cellulose acetate in an amount sufficient to inhibit or prevent the growth of a fungus on a surface coated with said surface coating composition. In one embodiment, the nanofibers are electrospun polyacrylonitrile nanofibers; in another embodiment, the nanofibers are electrospun cellulose acetate nanofibers. In another embodiment, the composition does not contain an antifungal agent selected from the group consisting of silver nanoparticles, polyene antifungals, azole antifungals, allylamine antifungals, or echinocandin antifungals.

In some aspects, the presently disclosed subject matter provides a method for the antifungal treatment of a surface comprising applying an antifungal effective amount of a composition comprising nanofibers of polyacrylonitrile and/or cellulose acetate to a surface in need of antifungal treatment. In one embodiment, the surface is contaminated with a fungus or was exposed to a fungus. In another embodiment, the antifungal treatment comprises slowing or preventing fungal growth on the surface. In one embodiment, the nanofibers are electrospun polyacrylonitrile nanofibers; in another embodiment, the nanofibers are electrospun cellulose acetate nanofibers. In another embodiment, the composition does not contain an antifungal agent selected from the group consisting of silver nanoparticles, polyene antifungals, azole antifungals, allylamine antifungals, or echinocandin antifungals.

In some aspects, the presently disclosed subject matter provides an antifungal surface treated with an antifungal effective amount of nanofibers of polyacrylonitrile and/or cellulose acetate. In one embodiment, the surface is porous, semi-porous or non-porous. In another embodiment, the surface is metal, wall board, ceiling tile, paper, textile, concrete, stone, brick, wood, plastic, ceramic, or leather. In another embodiment, the surface is a textile; in one variation, the surface is a garment, bedding or part of a shoe. In one embodiment, the nanofibers are electrospun polyacrylonitrile nanofibers; in another embodiment, the nanofibers are electrospun cellulose acetate nanofibers. In yet another embodiment, the surface is a fibrous material and the nanofibers are electrospun polyacrylonitrile nanofibers and/or electrospun cellulose acetate nanofibers. In another embodiment, the composition does not contain an antifungal agent selected from the group consisting of silver nanoparticles, polyene antifungals, azole antifungals, allylamine antifungals, or echinocandin antifungals.

In some aspects, the presently disclosed subject matter provides a surface coating composition comprising nanofibers of polyacrylonitrile or nanofibers of cellulose acetate. In one embodiment, the surface coating composition comprises nanofibers of polyacrylonitrile or nanofibers of cellulose acetate in an amount sufficient to inhibit or prevent the growth of a fungus on a surface coated with said surface coating composition. In another embodiment, the nanofibers are electrospun polyacrylonitrile nanofibers; in yet another embodiment, the nanofibers are electrospun cellulose acetate nanofibers.

In other aspects, the presently disclosed subject matter provides a method for the antifungal treatment of a surface comprising applying an antifungal effective amount of a composition comprising nanofibers of polyacrylonitrile or nanofibers of cellulose acetate to a surface in need of antifungal treatment. In one embodiment, the surface is contaminated with a fungus; in another embodiment, the surface was exposed to a fungus; in yet another embodiment, the surface will be exposed to a fungus; in a further embodiment, the surface is at risk of being exposed to a fungus. In one embodiment, the nanofibers are electrospun polyacrylonitrile nanofibers; in another embodiment, the nanofibers are electrospun cellulose acetate nanofibers.

In still other aspects, the presently disclosed subject matter provides a method for slowing or preventing fungal growth on a surface comprising applying to the surface a composition comprising nanofibers of polyacrylonitrile or nanofibers of cellulose acetate. In one embodiment, the composition comprises an antifungal effective amount of electrospun polyacrylonitrile nanofibers; in another embodiment, the composition comprises an antifungal effective amount of electrospun cellulose acetate. In one embodiment, the surface is contaminated with a fungus; in another embodiment, the surface was exposed to a fungus; in yet another embodiment, the surface will be exposed to a fungus; in a further embodiment, the surface is at risk of being exposed to a fungus.

In one variation of any of the disclosed aspects or embodiments, the composition comprising nanofibers of polyacrylonitrile or nanofibers of cellulose acetate is a solution or a film. In one such variation, the composition is a paint comprising electrospun polyacrylonitrile nanofibers or electrospun cellulose acetate nanofibers.

In some embodiments, the presently disclosed subject matter provides an antifungal surface treated with an antifungal effective amount of nanofibers of polyacrylonitrile or cellulose acetate. In some embodiments, the nanofibers are electrospun polyacrylonitrile nanofibers; in other embodiments, the nanofibers are electrospun cellulose acetate nanofibers.

In one variation of any of the disclosed aspects or embodiments, electrospun polyacrylonitrile nanofibers and/or electrospun cellulose acetate nanofibers are the only antifungal components of the antifungal composition. In yet another embodiment, electrospun polyacrylonitrile nanofibers are the only antifungal component of the antifungal composition; in an alternate embodiment, electrospun cellulose acetate nanofibers are the only antifungal component of the antifungal composition.

In one variation of any of the disclosed aspects or embodiments, the disclosed composition comprising nanofibers of polyacrylonitrile and/or nanofibers of cellulose acetate does not include any other agent with antifungal activity. Such known antifungal agents include silver nanoparticles, as well as chemical agents, including but not limited to polyene antifungals (e.g. amphotericin B), azole (e.g. imidazole, triazole or thiazole) antifungals, allylamine antifungals, or echinocandin antifungals. In other embodiments, the composition includes another antifungal agent disclosed herein. In still other embodiments, the composition includes a chemical antifungal agent, such as an azole antifungal or an echinocandin antifungal.

In one variation of any of the disclosed aspects or embodiments, the surface is porous, semi-porous or non-porous. In yet another variation, the surface is an indoor or outdoor surface. In another variation, the surface includes, but is not limited to metal, wall board, ceiling tile, paper, textile, concrete, stone, brick, wood, plastic, ceramic, and leather. In some embodiments, the surface is a garment, bedding, part of a shoe or a shoe insole. In some variations, the surface is a shoe insole, which is replaceable or is permanently attached to the shoe. In another variation, the surface is a textile, including, but not limited to a non-woven textile or a woven textile or a natural or synthetic textile. In yet another variation, the surface is a garment, such as medical scrubs, socks, hosiery, a mask, a lab coat or a glove. In another variation, the surface is a type of bedding, such as, but not limited to, pillow, pillowcase, sham, comforter, quilt, duvet cover, throw, mattress pad, sheet, blanket, mattress topper, or mattress protector. In another variation, the surface is a floor, a wall, a sink, a table, a bucket, or a countertop.

As disclosed herein, application to a surface can include incorporation of the nanofibers disclosed herein into the material comprising the surface, such as, for example, a porous or semi-porous surface or woven textile. In each material, the nanofiber-containing composition can occupy void space in the material, thus providing nanofiber antifungal functionality to otherwise unused space. Such 'internal' as well as 'external' distribution of the nanofibers can increase the capacity to control fungal cell growth by increasing the total amount of nanofibers in the product, yielding nanofibers distributed not only on the surface, but also within the material.

In one variation of any of the disclosed aspects or embodiments, the nanofibers have an average diameter of between about 100 nm and 1000 nm or between about 300 nm and about 700 nm or between about 400 nm and about 600 nm. In another embodiment, the nanofibers have an average diameter of no more than about 1000 nm, of no more than about 750 nm, of no more than about 500 nm.

In one variation of any of the disclosed aspects or embodiments, the nanofibers of polyacrylonitrile or cellulose acetate can be combined with one or more other antifungal agents, such as a chemical agent, including but not limited to polyene antifungals (e.g. amphotericin B), azole (e.g. imidazole, triazole or thiazole) antifungals, allylamine antifungals, or echinocandin antifungals or antifungal agents such as silver nanoparticles.

As described further hereinbelow, nanofibers described herein can be made in any manner not inconsistent with the objectives of the present disclosure. The nanofibers may especially advantageously be made by electrospinning as disclosed herein.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

1. Materials

Polyacrylonitrile (PAN), Cellulose acetate (CA), N,N-Dimethylformamide (DMF), sodium phosphate dibasic ($Na_2HPO_4$) and sodium phosphate monobasic ($NaH_2PO_4$) were purchased from Sigma-Aldrich (St. Louis, Mo., USA). PAN microfibers, having an average fiber diameter of about 10 µm, were purchased from Xi'an Zhongrun Architectural Technology Corporation (China). S. Cerevisiae yeast strain SK1 (ATCC stock number: 204722; genotype: MATalMA-Talpha HO can1(r) gal2 cup (s)), S. cerevisiae yeast strain W303 (ATCC stock number: 208352; genotype: MATaade2-1ura3-1 his3-11trp1-1leu2-3leu2-112can1-100) were obtained from American Type Culture Collection), and C. albicans yeast strain, (ATCC stock number 10231) were obtained from American Type Culture Collection. Paraformaldehyde was purchased from Ted Pella, Inc. (Redding, Calif., USA). Phosphate buffered saline (PBS) is prepared by mixing 1 M $NaH_2PO_4$ and 1 M $Na_2HPO_4$ aqueous solutions at pH=7.4.

2. Substrate Preparation

Polyacrylonitrile (PAN) nanofibers with an average diameter of about 500 nm were obtained by electrospinning 10 wt % PAN solution in dimethylformamide at a voltage of 15 KV and feeding rate of 1.0 ml/hr. PAN solid films were obtained by casting the PAN spinning solution onto a TEFLON® plate and drying at room temperature. PAN microfibers were rinsed with acetone and then were randomly stuck together with a small amount of DMF to make a nonwoven microfibrous mat.

Cellulose acetate (CA) nanofibers were obtained by electrospinning a solution comprising 20 wt. % cellulose acetate in a mixture solvent of 1:1 tetrahydrofuran and dimethyl sulfoxide plus trace amount of sodium citrate at a rate of 1.2 ml/hr and a voltage of 22 KV. The electrospun nanofibers were collected over rotating drum collector and good homogenous fibers were obtained. Cellulose acetate solid films were obtained by casting the CA spinning solution onto a TEFLON® plate and drying at room temperature.

Cellulose nanofibers were prepared by treating cellulose acetate nanofibers with 0.05 M NaOH overnight and rinsing the resulting cellulose nanofibers and then drying. Cellulose films were obtained by treating a cellulose acetate film with 0.05 M NaOH overnight and rinsing the resulting cellulose film and drying at room temperature.

3. Cell Culture 3.1 SK1 Cell Growth

SK1 cells were grown overnight in 20 ml Yeast extract, Peptone, and Dextrose medium (YPD, which provides the source of amino acids, nucleotide precursors, vitamins, and metabolites for cell growth) in a shaking incubator at 200 r.p.m at room temperature for 18 hours. The culture was diluted in the next day to $OD_{600}$=0.1-0.16 then left to grow at 28° C. in a shaking incubator at 200 r.p.m to mid log phase of growth ($OD_{600}$=0.4-0.6).

3.2 W303 Cell Growth

W303 cells were grown overnight in 5 ml yeast extract, peptone, and dextrose medium (YPD, the source of amino acids, nucleotide precursors, vitamins, and metabolites that are needed for cell growth) in a shaking incubator at room temperature for 24 hours. The culture was diluted with 45 ml YPD the next day. The culture medium was maintained in the incubator until the yeast strains grew to mid log phase ($OD_{600}$=~0.4).

3.3 C. albicans Cell Growth

C. albicans cells were cultured on Sabouraud Dextrose Agar (SBD) solid agar plate for 48 hrs in an incubator at 30° C. and stored in a refrigerator for 3 days before use, as disclosed herein.

4. Characterization 4.1. Cell and substrate morphology

PAN solid film, PAN microfibrous mat, and PAN nanofibrous mat were cut into 6 mm×4 mm pieces and glued to glass chips respectively. The glass chips were further individually glued onto petri dishes. Culture of SK1 strains or W303 strains was then transferred to corresponding petri dishes. After 30 min contact, the substrates were rinsed softly with DI water and placed in paraformaldehyde fixing solution. These samples were taken out of fixing solution after overnight immersion and left to dry at room temperature with the aid of DRIERITE™ desiccant. Morphology of SK1 cells, W303 cells, and substrates were examined by a Carl Zeiss Auriga-BU FIB field emission scanning electron microscope. Before SEM imaging, all surfaces were sputter-coated with gold to avoid charge accumulation.

4.2. Colony Forming Units (CFU)

Population of cell in SK1 culture was characterized by measuring light absorption of the culture at wavelength of 600 nm ($OD_{600}$). SK1 cells were cultured overnight to $OD_{600}$=~1.8 and then diluted to $OD_{600}$=0.1 and $OD_{600}$=0.05, respectively. PAN solid film, microfibrous mat, and nanofibrous mat were cut into approximately 3.5 cm×2.2 cm pieces and placed individually in a well on a six-well culture plate. 6 ml SK1 cell culture at $OD_{600}$=0.1 or $OD_{600}$=0.05 were then transferred respectively into corresponding wells including one empty well for control purpose. CFU experiments were conducted with the two respective SK1 cultures under mechanical shaking. Mechanical shaking was done after the cell culture plate was placed in a shaker that was set at 150 r.p.m. Mechanical shaking was performed in order to avoid large cell deposition on substrates. After 1 hour incubation, cell cultures were removed from respective well and underwent a series of dilutions. 100 µl of respective final cell culture dilution were taken out and spread onto a petri dish with solid agar. Corresponding agar petri dish was incubated at 26° C. for 48 hours before cell colonies were counted manually. CFU assays were repeated three times for each substrate and the results were analyzed statistically by using t test calculator from GRAPHPAD™ software.

4.3. Optical Density Test

In optical density test, SK1 cells were cultured overnight and then diluted to one tenth and one hundredth, respectively. Two pieces of PAN nanofibrous mats (10 mg) were cut from the electrospun product and placed in a 70 ml flask, respectively. 20 ml YBD media plus 20 µl of respective diluted cell culture were then poured into each flask. The same amount of YBD media and respective diluted cell cultures without PAN nanofibrous mats were placed in another two flasks and served as control samples. These flasks were then placed in a shaking incubator at 26° C. for 18 hours before OD test. $OD_{600}$ of all these SK1 cell cultures was characterized through a Thermo Scientific NANO-DROP™ 2000C spectrophotometer. The above-described optical density test was repeated three times with fresh PAN nanofibrous mats for each diluted cell culture and average OD data were reported.

4.4. Live/Dead Cells Viability (In Vitro) Assays

SK1 cells were cultured overnight and 10 ml of the culture was taken out for test and then 10 µl acridine orange (10 mg/ml) was added into the cell culture. The culture was then diluted to $OD_{600}$=0.1 by using mixture of propidium iodide (5 mg/ml) and YPD media at volume ratio 1:1000. PAN nanofibrous mat (approximately 6 mm×4 mm) was introduced to the culture mixture and the whole system was incubated for 10 minutes prior to confocal imaging of the PAN nanofibrous mat by Zeiss Axiom Plan spinning disc confocal microscope. Fluorescent images from the confocal microscope were processed by Image J software for cell counting.

Example 1

Effect of Different PAN Materials on Growth of Fungal Cells, SK1

Figure 1B:
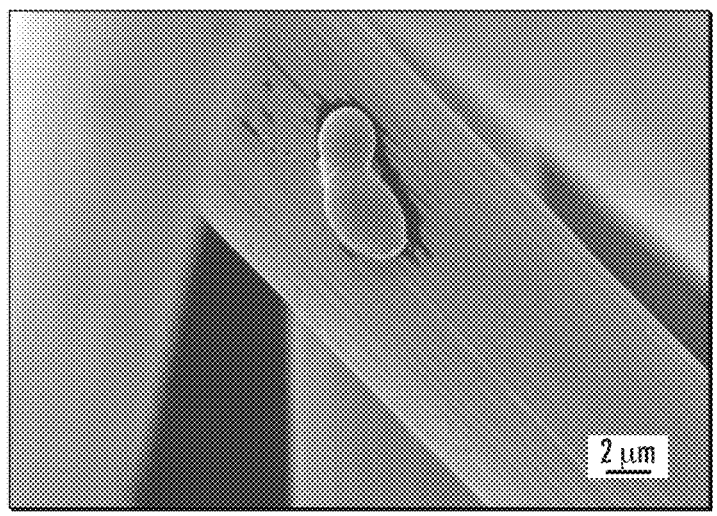
FIG. 1B illustrates an SEM image of yeast cells cultured on a PAN substrate after 30 min incubation wherein the PAN substrate is a microfibrous mat.
Figure 1C:
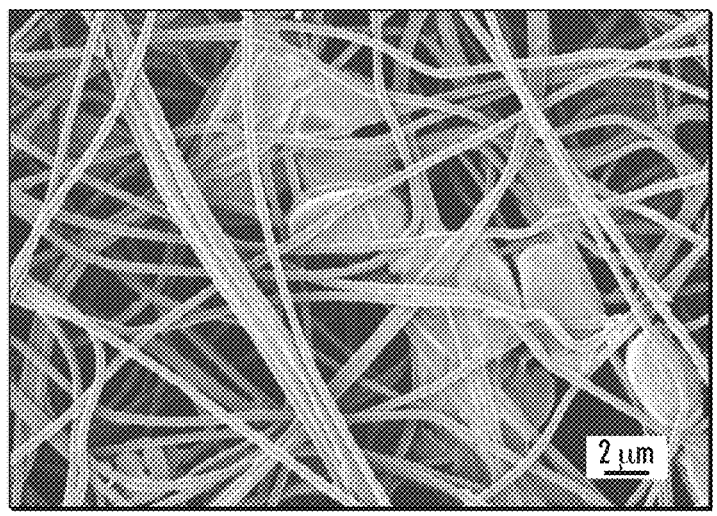
FIG. 1C illustrates an SEM image of yeast cells cultured on a PAN substrate after 30 min incubation wherein the PAN substrate is a nanofibrous mat.

To investigate the interaction between yeast cells and electrospun PAN nanofibrous mat, S. cerevisiae yeast strain SK1 was cultured and applied to each of a PAN nanofibrous mat, a PAN film and a PAN microfibrous mat. The PAN nanofibrous mat was prepared by electrospinning PAN fibers with average diameter of ~500 nm, while the PAN microfibrous mat was comprised of fibers having an average diameter of about 10 μm. The PAN film was prepared via solution casting and the resultant films showed a solid but somewhat crimpled surface. SK1 cells grew normally upon 30 min contact with the PAN film and PAN microfibrous mat and generally grew bigger as they aged (FIGS. 1A and 1B). On these control surfaces, mid-log phase growth SK1 cells exhibited an ellipsoidal shape with varied sizes in the range of 3-4 micrometers, characteristic of normal healthy cells. However, SK1 yeast cells exhibited a distinctly flattened, abnormal, morphology after only 30 minutes incubation exposure to the electrospun PAN nanofibrous mat (FIG. 1C). Cell morphology studies suggest that the PAN nanofibrous mat inhibit yeast cell growth without needing any external aid such as antifungal agents, indicating a valuable antifungal functionality of electrospun PAN nanofibrous mats.

To determine whether (a) malformed SK1 cells were bound to the electrospun PAN nanofibrous mat and exhibited reduced viability or (b) SK1 cells' membrane became compromised due to contact with electrospun PAN nanofibrous mat, two additional experiments were performed—a colony forming assay (CFU) and a mitochondrial morphology/membrane potential assay.

Figure 2:
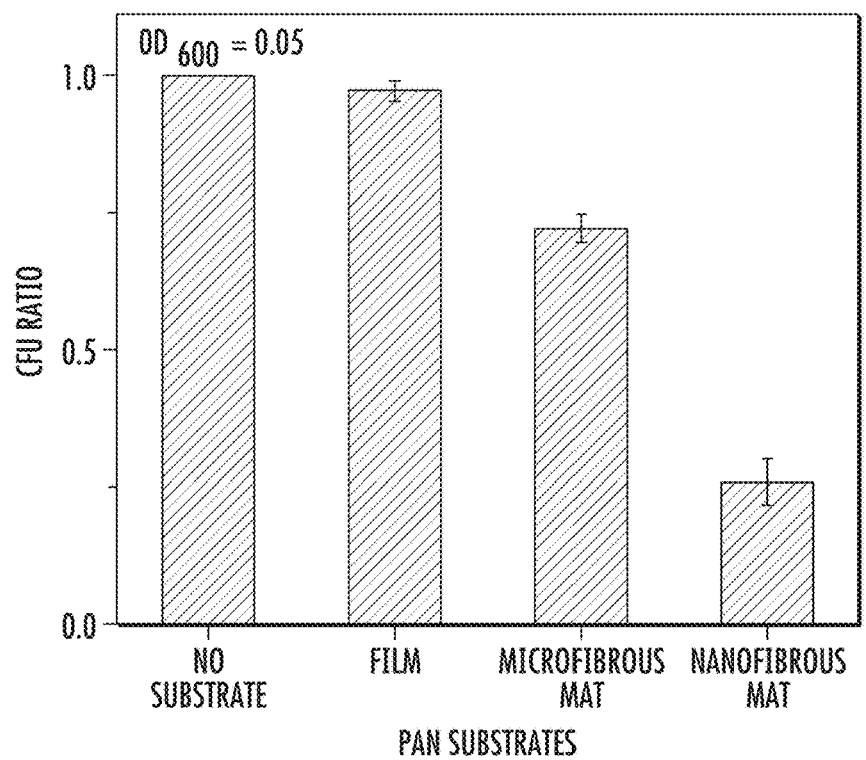
FIG. 2 is a bar graph showing the effect of different PAN substrates on SK1 cell growth as represented by colony forming units (CFUs) starting at $OD_{600}$=0.05 after incubation. The measured CFU of each sample was normalized according to the CFU of SK1 culture without substrate (left bar) and the data are shown as a CFU ratio.

CFU is a standard biological assay that measures the number of live microbes in a unit volume (colony units per milliliter). To assess the viability of yeast on electrospun nanofibrous mat, a CFU experiment was performed with SK1 strain culture at $OD_{600}$=0.05 (~1.5 ×$10^6$ cells/ml). Optical Density of all SK1 cell cultures was characterized using a NANODROP™ 2000C spectrophotometer (ThermoFischer Scientific, Waltham, Mass. USA). $OD_{600}$ is commonly used to characterize cell population per culture volume by measuring light absorption of cell culture at wavelength of 600 nm. After 1 hour contact and incubation, a significant (66%) reduction in the number of cells incubated with the electrospun PAN nanofibrous mat was observed compared to (a) control including no substrate, (b) incubated with a PAN film, and (c) incubated with a PAN microfibrous mat (FIG. 2). As shown, PAN nanofibrous mat was capable of significantly inhibiting yeast cell survival and growth.

$OD_{600}$ of the SK1 cell cultures was examined with and without an electrospun PAN nanofibrous mat during incubation. To perform these experiments, starting SK1 cultures ($OD_{600}$=1.83) were diluted to a high cell concentration ($OD_{600}$=0.37) and low cell concentration ($OD_{600}$=0.04) in YPD nutrient solution, with or without 10 mg nanofibrous PAN and incubated for 18 hours. Optical densities of the cell cultures were measured. (Table 1) In control cultures (without nanofibrous PAN), $OD_{600}$ of both the high cell concentration and the low cell concentration grew robustly. In the high cell concentration control culture $OD_{600}$ increased from 0.37 to 2.2. In the presence of nanofibrous PAN, however, $OD_{600}$ dropped from 2.2 to 0.5. In the culture started with fewer cells, $OD_{600}$ reduction was even more pronounced. In the presence of nanofibrous PAN, zero optical density ($OD_{600}$=0) was recorded, compared to 0.3 for the corresponding low cell concentration control. (Table 1)

TABLE 1

$OD_{600}$ of SK1 cell cultures incubated with or without electrospun PAN nanofibrous mat

| Before incubation Starting culture | After incubation | |
|---|---|---|
| | Control culture | Culture with electrospun PAN nanofibrous mat |
| 0.37 | 2.2 | 0.5 |
| 0.04 | 0.3 | 0.0 |

The CFU and $OD_{600}$ results were consistent with changes in cell morphology. To investigate the effect of nanofibrous PAN on the integrity of the yeast cell, mitochondrial morphology/membrane potential assay (commonly known as live/dead cell assay) was conducted by using a mixture of two nucleic acid fluorescent stains, propidium iodide (PI) and acridine orange (AO). PI has maximum excitation at 535 nm and maximum emission at 617 nm. PI is the basis of cell viability through this standard live/dead essay. PI is a cell impermeable dye, but enters cell through ruptured cell membranes and binds with DNA, emitting red radiation. AO has maximum excitation at 488 nm and maximum emission at 518 nm. AO can permeate into nucleated cells, bind with DNA and emit green radiation. Confocal laser scanning microscopy (CLSM) is a fluorescence microscopy used to view emitted radiations from live/dead cells, in which red spots indicate dead cells and green spots indicate live cells. In the live/dead cell assay, a PAN nanofibrous mat was introduced to SK1 cell culture with AO and PI and the whole system was incubated for 10 min. Based on an analysis of the fluorescent images of PAN nanofibrous mat after incubation, 74% SK1 cells emitted red radiation, indicating loss of viability. Thus nanofibrous PAN hindered cell viability within 10 min of contact. SK1 cells were all alive (100%) on PAN film after the same time contact. The live/dead cell assay confirmed that most of yeast cells on the surface of PAN nanofibrous mat were dead, consistent with the CFU and $OD_{600}$ measurements.

Figure 4:
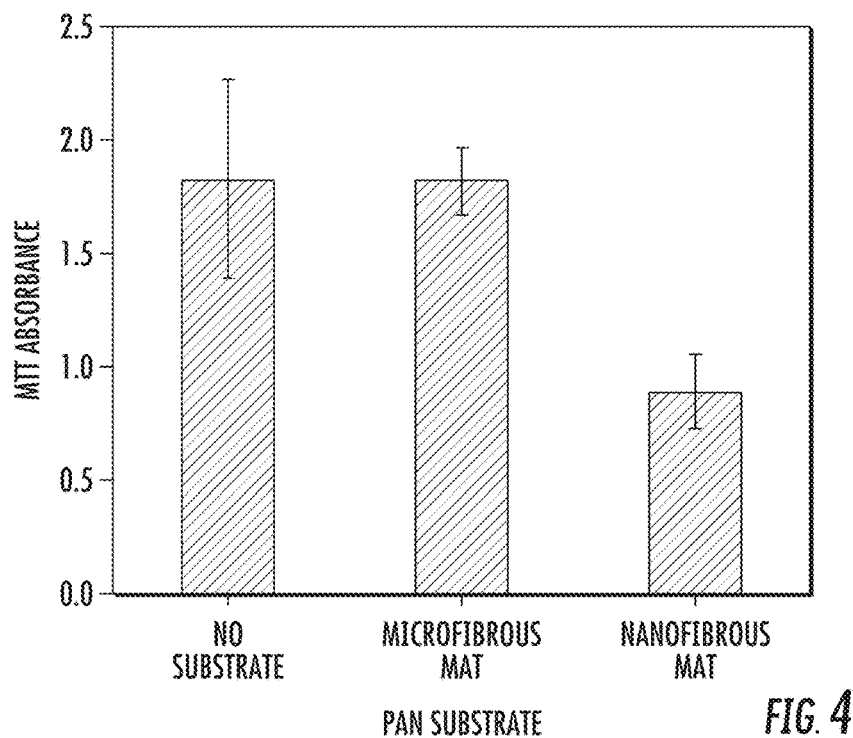
FIG. 4 is a graph showing the effect different PAN substrates (nanofibrous mat, solid film, microfibrous mat and control without a PAN substrate) on SK1 cell growth after an eight hour incubation, as represented by the optical density ($OD_{600}$).

*S. cerevisiae* SK1 cell growth in cultures with a PAN nanofibrous mat during first 8 hours was investigated. Normally the number of cells in a culture solution continues to increase with incubation time when enough nutrient is present. The blank control of SK1 culture as well as SK1 cultures with PAN film and PAN microfibrous mat showed a similar optical density growth profile versus time (FIG. 4). The growth profile of the SK1 culture with a PAN nanofibrous mat significantly deviated from that of the blank control. A much lower optical density was observed for the cell culture with PAN nanofibrous mat. The cell number drop at the beginning of the 8th hour was notable. The lower SK1 cell growth profile with PAN nanofibrous mat, as well as the cell number drop, is consistent with the immediate inhibition of yeast cell growth upon contact with the PAN nanofibrous mat. Without being bound by theory, if cell retention by the PAN nanofibrous mat had been observed, there would have been a large cell number increase after first couple of hours due to cells entering the culture solution due to mechanical shaking and the 'freed' cells would be expected to thereafter grow robustly.

Figure 5:
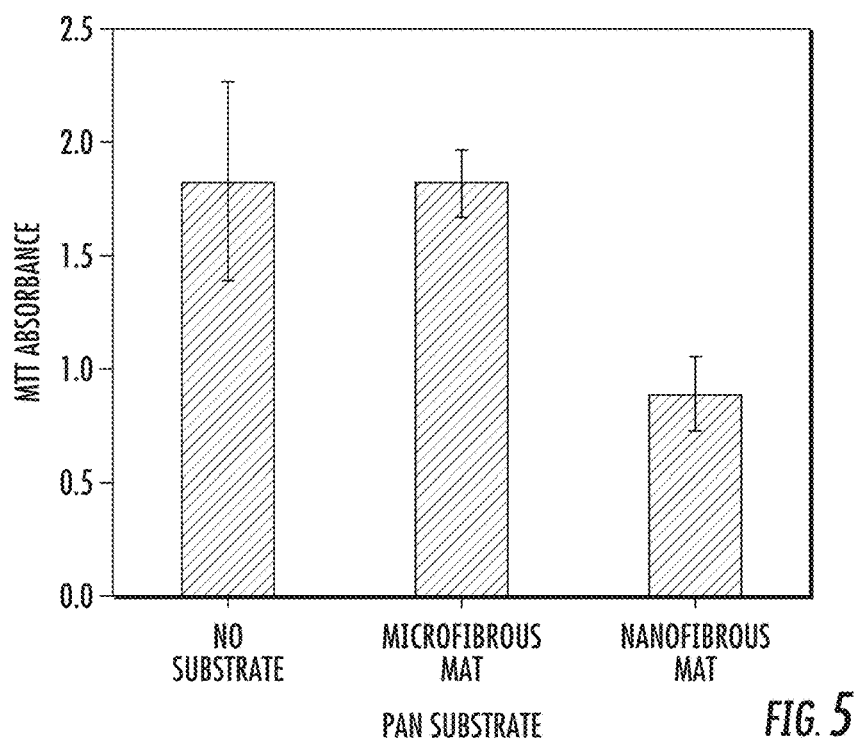
FIG. 5 is a graph showing the effect of different PAN substrates (no substrate, PAN microfibrous mat and PAN nanofibrous mat) on the growth of SK1 cells after incubation, as represented by MTT absorbance.

The CFU and optical density results were consistent with observed changes in cell morphology and growth inhibition of yeast cells by the PAN nanofibrous mat. To explore cell viability directly on a PAN nanofibrous mat, a colorimetric assay for assessing SKl cell metabolic activity was performed using a tetrazolium dye (3-(4,5-dimethylthiazol-2-yl)-2,5-diphenyltetrazolium bromide (MTT assay). Reduction of tetrazoium salts is widely accepted as a reliable way to examine cell proliferation. MTT is reduced by metabolically active cells and the purple formazan product can be quantified by spectrophotometry. SK1 cells exposed to a PAN nanofibrous mat showed much lower MTT absorbance (FIG. 5) compared to SK1 cells exposed to a PAN microfibrous mat or to no substrate. Based on the MTT results, SKI cells with a PAN nanofibrous mat showed much lower metabolic activity as well as a lowered proliferation rate, consistent with the inhibiting role of PAN nanofibrous mat when in contact with fungal cells.

Figure 6:
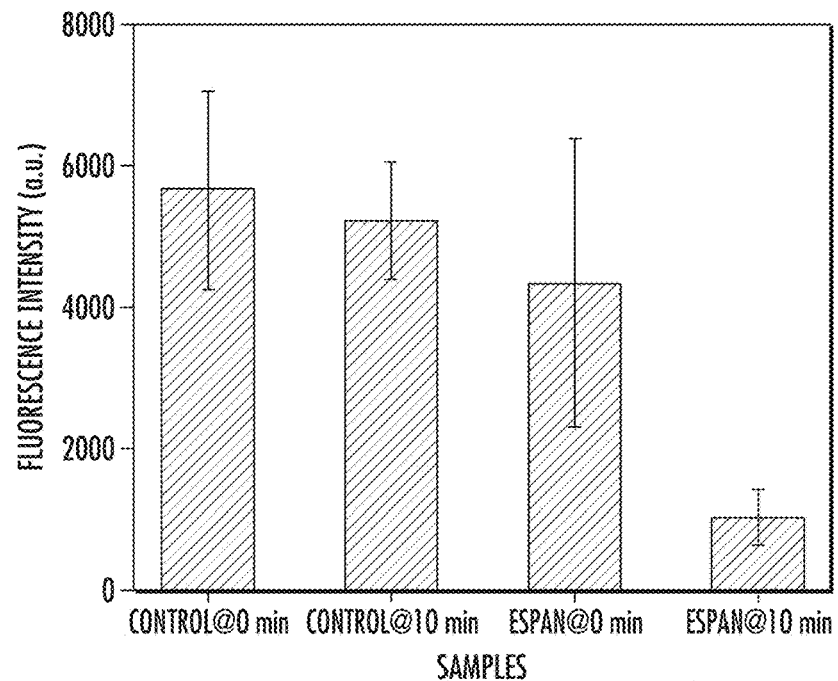
FIG. 6 is a graph of variation in fluorescence intensity of MitoTracker Red stained SK1 cells compared to control after 0 and 10 minutes exposure to a PAN nanofibrous mat (ESPAN).

A red-fluorescent dye, MitoTracker Red FM, was used to characterize SK1 cells viability. When cells are incubated with the cell-permeable MitoTracker Red, the dye passively diffuses across live cells' plasma membrane and accumulates in active mitochondria. Low intensity of fluorescence emission observed therefrom is an indication of low mitochondrial membrane potential and low mitochondrial membrane potential correspondingly indicates apoptosis induction in cells. Compared to a blank control sample, a significant fluorescence intensity reduction of MitoTracker Red stained SK1 cells on PAN nanofibrous mat was observed after 10 min contact (FIG. 6). Thus, without being bound by theory, it is presumed that SK1 cells became much less metabolically active or severely stressed on PAN nanofibrous mat. It was noteworthy that PAN nanofibrous mat could significantly inhibit cell's viability as soon as 10 min contact.

The combined experimental results demonstrated that nanofibrous PAN has an intrinsic antifungal activity. Compared to PAN film and PAN microfibrous mat, each of which provide solid support to yeast cells, it was observed that nanofibrous PAN provided limited and asymmetrical contact to the yeast cells. Without being bound by theory, yeast cells may experience differentiated adhesion between different parts of the cell and adjacent PAN nanofibers, thereby inducing internal tension. Interaction of yeast cells with the PAN nanofibrous mat resulted in lower cell metabolic activity, lower proliferation and eventually cell rupture and/or cell death.

Example 2

Effect of Different Nanofibrous Mats on SK1 Cell Growth Via Optical Density Test To evaluate whether the effect of nanofibrous PAN was due solely to the size of the electrospun fibers, different nanofibrous mats were prepared and the growth of SK1 cells on the different nanofibers were evaluated.

In this study, SK1 cells were cultured overnight and then diluted to one tenth ($OD_{600}$=0.37) and one hundredth ($OD_{600}$=0.04)), respectively. Samples of electrospun nanofibrous mats (10 mg) of each of: PAN, amidoxime surface modified PAN, carbon, cellulose, cellulose acetate, cellulose with embedded $TiO_2$ (Cellulose_$TiO_2$), and cellulose acetate with embedded $TiO_2$ (CA_$TiO_2$) mats were placed in a 70 ml flasks, respectively. YBD media (20 mL) plus 20 μl of diluted SK1 cell cultures were poured into each flask. The control sample was prepared with 20 mL YBD media and 20 μl of diluted SK1 cell culture without nanofibrous mats in another flask. The flasks were then placed in a shaking incubator at 26° C. for 18 hours before conducting an Optical Density test at 600 nm ('$OD_{600}$'). $OD_{600}$ of all SK1 cell cultures was characterized using a NANODROP™ 2000C spectrophotometer (ThermoFischer Scientific, Waltham, Mass. USA). The optical density test was repeated three times with fresh nanofibrous mats for each diluted cell culture and average OD data calculated. (Table 2 and Table 3) As shown, nanofibrous cellulose acetate demonstrated notable antifungal activity compared to control.

TABLE 2

$OD_{600}$ of SK1 strain after 18 hr contact with electrospun nanofibrous mats (starting $OD_{600}$ = 0.37)

| PAN | ASFPAN | Cellulose | Cellulose_$TiO_2$ | CA | CA_$TiO_2$ | Carbon | Control |
|---|---|---|---|---|---|---|---|
| 0.50 | 1.54 | 1.4 | 1.61 | 0.91 | 1.98 | 2.0 | 2.2 |

TABLE 3

$OD_{600}$ of SK1 strain after 18 hr contact with electrospun nanofibrous mats (starting $OD_{600}$ = 0.04)

| PAN | ASFPAN | Cellulose | Cellulose_$TiO_2$ | CA | CA_$TiO_2$ | Carbon | Control |
|---|---|---|---|---|---|---|---|
| 0 | 0.12 | 0.2 | 0.36 | 0.026 | 0.14 | 0.44 | 0.30 |

Example 3

Effect of Nanofiber Mat on SK1 and W303 Cell Growth Via SEM

To confirm that the antifungal activity of nanofibrous PAN was not unique to SK1, but instead representative of a broader class of fungal cells, the growth of SK1 and W303, a S. cerevisiae yeast strain, was compared via scanning electron microscopy.

Figures 3A, 3B:
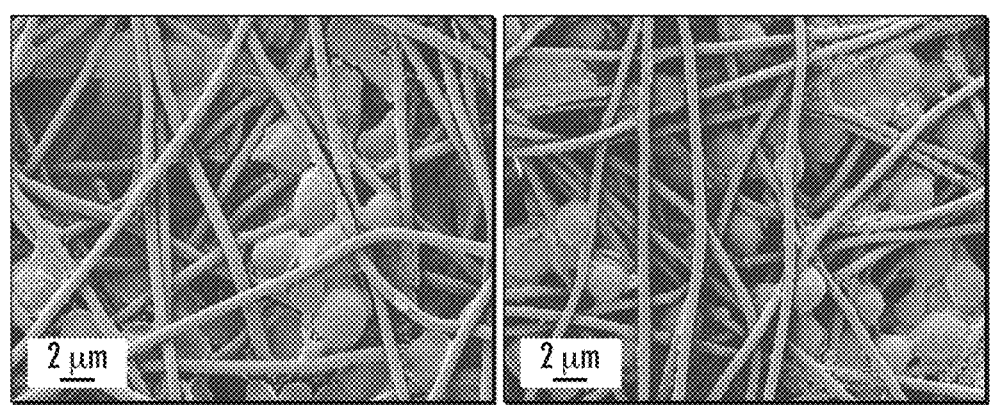
FIG. 3A illustrates an SEM image of images of SK1 yeast cells cultured on PAN nanofibrous mat after 30 min contact.
FIG. 3B illustrates an SEM image of images of W303 yeast cells cultured on PAN nanofibrous mat after 30 min contact.

Nanofibrous PAN mats were cut into 6mm×4 mm pieces and glued individually to glass chips. The glass chips were then glued onto petri dishes. Cultures of SK1 and W303 strains were transferred into corresponding petri dishes. After 30 minutes of contact, the nanofibrous samples were rinsed softly with DI water and immersed in a fixing solution. The samples were then removed from solution after overnight immersion and left to dry. The samples were evaluated using SEM imaging. Both SK1and W303 cells flattened and lost their vitality after 30 min contact with the surface of nanofibrous PAN (FIGS. 3A and 3B).

Example 4

Effect of PAN and CA Nanofibers on the Growth of Fungal Cells, SK1 and C. Albicans Fungal cells, SK1 and *C. albicans*, were cultured on YPD and SBD solid agar plates, respectively, for 48 hrs in an incubator at 30° C. and stored in a refrigerator for 3 days. Different mass of substrates including 25 mg, 20 mg, 15 mg, 10 mg and 5 mg of each of CA nanofibrous mat, PAN nanofibrous mat, cellulose nanofibrous mat, CA film, PAN film, cellulose film were added to individual 50 mL glass flasks. 10 ml YPD and SBD liquid media were added to the corresponding 50 mL glass flasks for SK1 and *C. albicans*, respectively. One 5-day-old single colony of either SK1 and *C. albicans* was selected from the relevant solid agar plate and added to the respective flasks. The flasks were then placed in a shaking incubator (130 rpm) at 25° C. for 16 hours. Optical densities ($OD_{600}$) were measured afterwards by a Thermo Scientific NANODROP™ 2000C spectrophotometer.

Figure 7A:
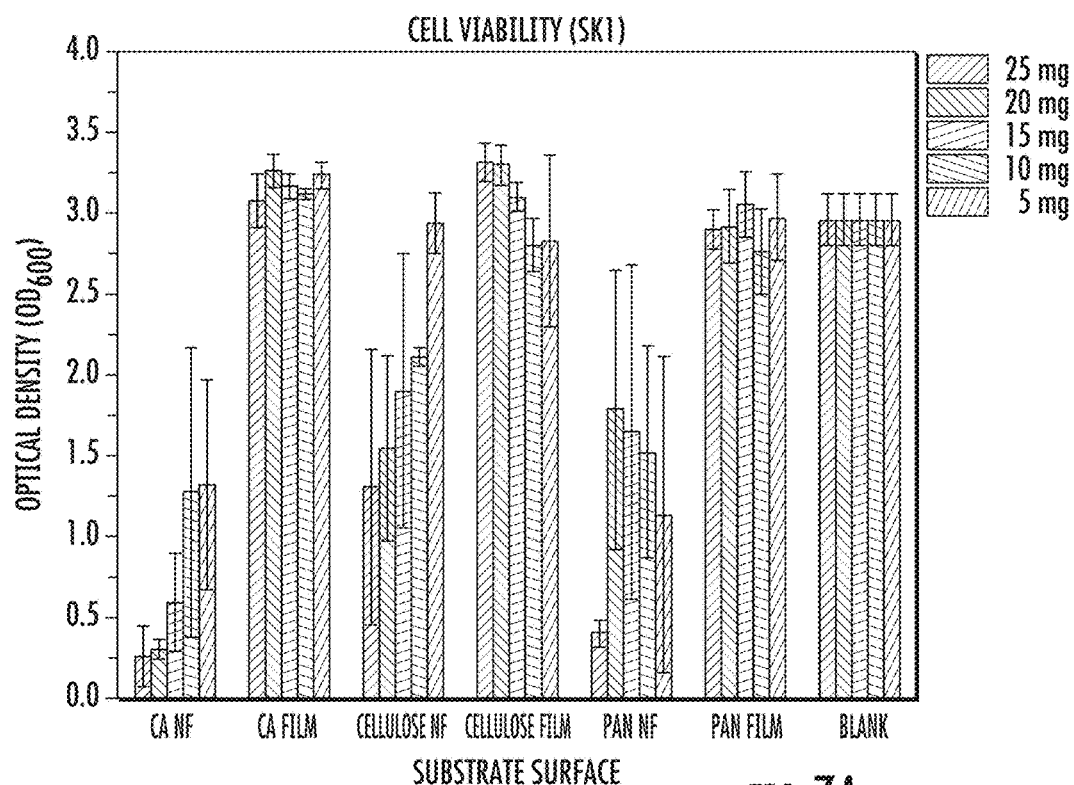
FIG. 7A is a graph showing the effect of different masses of substrates: CA nanofibrous mat, CA film, cellulose nanofibrous mat, cellulose film, PAN nanofibrous mat, PAN film and control on the growth of SK1 cell cultures after 16 hour incubation, as represented by optical density ($OD_{600}$).
Figure 7B:
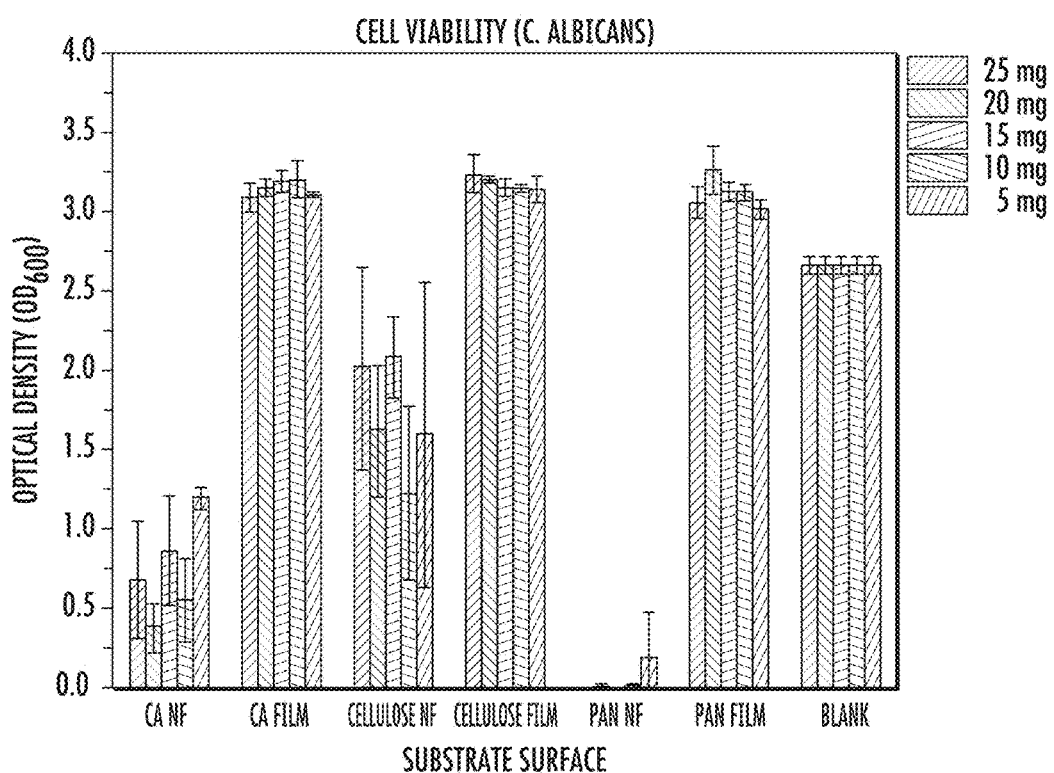
FIG. 7B is a graph showing the effect of different masses of substrates: CA nanofibrous mat, CA film, cellulose nanofibrous mat, cellulose film, PAN nanofibrous mat, PAN film and control on the growth of C. albicans cell cultures after 16 hour incubation, as represented by optical density ($OD_{600}$).

The $OD_{600}$ results (FIG. 7) clearly showed that electrospun nanofiber mats including CA, cellulose and PAN have differing inhibition effects on the growth of SKI and *C. albicans*. Particularly PAN and CA nanofibrous mats showed much stronger inhibition effect than cellulose nanofibrous mat. For SKI cells, the CA nanofibrous mat had a more significant inhibition effect than that of the PAN nanofibrous mat. For *C. albicans*, the PAN nanofibrous mat had a more significant inhibition effect than the CA nanofibrous mat. The control substrates, and cast films of CA, cellulose and PAN didn't show an inhibition effect. Instead, the films appeared to promote fungal cell growth. As the mass of the nanofibrous mat increased, its inhibition affect generally increased correspondingly.

It will be understood that various details of the presently disclosed subject matter may be changed without departing from the scope of the presently disclosed subject matter. Furthermore, the foregoing description is for the purpose of illustration only, and not for the purpose of limitation.

The invention claimed is:

1. A method for the antifungal treatment of a surface comprising: providing a surface exposed to a fungus or contaminated with a fungus; and applying a composition comprising an antifungal effective amount of nanofibers of polyacrylonitrile having antifungal activity to the surface, wherein the antifungal effective amount is an amount sufficient to inhibit growth of fungus on the surface and such that the optical density at 600 nanometers ($OD_{600}$) of a solution of fungi exposed to the nanofibers of polyacrylonitrile of the composition is no more than about 75% of the $OD_{600}$ of a solution of fungi not exposed to said nanofibers, wherein the nanofibers of polyacrylonitrile are the only components of the composition that have the antifungal activity.

2. The method of claim 1, wherein the antifungal treatment comprises inhibiting or preventing fungal growth on the surface.

3. The method of claim 1, wherein the nanofibers are electrospun polyacrylonitrile nanofibers.

4. The method of claim 1, wherein the surface is porous, semi-porous or non-porous.

5. The method of claim 1, wherein the surface is metal, wall board, ceiling tile, paper, textile, concrete, stone, brick, wood, plastic, ceramic, or leather.

6. The method of claim 1, wherein the surface is a textile.

7. The method of claim 1, wherein the surface is a garment, bedding, or a part of a shoe.

8. The method of claim 5, wherein the nanofibers are electrospun polyacrylonitrile nanofibers.

9. The method of claim 1, wherein the surface is a fibrous material and the nanofibers are electrospun polyacrylonitrile nanofibers.

10. The method of claim 6, wherein the nanofibers are electrospun polyacrylonitrile nanofibers.

* * * * *